United States Patent [19]

LoCicero, III

[11] Patent Number: 5,887,594
[45] Date of Patent: Mar. 30, 1999

[54] METHODS AND DEVICES FOR GASTROESOPHAGEAL REFLUX REDUCTION

[75] Inventor: Joseph LoCicero, III, Dover, Mass.

[73] Assignee: Beth Israel Deaconess Medical Center Inc., Boston, Mass.

[21] Appl. No.: 935,241

[22] Filed: Sep. 22, 1997

[51] Int. Cl.[6] .............................. A61B 19/00; A61B 1/22; A61B 17/34
[52] U.S. Cl. .......................... 128/898; 600/201; 606/185
[58] Field of Search ............................ 128/898; 600/201, 600/210; 606/1, 151, 157, 167, 185

[56] References Cited

U.S. PATENT DOCUMENTS

| | | | |
|---|---|---|---|
| 3,875,928 | 4/1975 | Angelchik . | |
| 4,271,827 | 6/1981 | Angelchik . | |
| 4,271,828 | 6/1981 | Angelchik . | |
| 5,006,106 | 4/1991 | Angelchik | 600/37 |
| 5,423,821 | 6/1995 | Pasque | 606/151 |
| 5,456,246 | 10/1995 | Schmieding et al. | 606/151 |
| 5,573,496 | 11/1996 | Mcpherson et al. | 600/210 |

OTHER PUBLICATIONS

Thibault, Claude et al., *The Angelchik Antireflux Prosthesis: Long–Term clinical and Technical Follow–up*, Canadian Journal of Surgery, vol. 37, No. 1, Feb. 1994.

*Primary Examiner*—Glenn K. Dawson
*Attorney, Agent, or Firm*—Lahive & Cockfield, LLP

[57] ABSTRACT

Methods for reducing gastroesophageal reflux are provided. One method includes passing a piercing device into the esophagus of a patient. The piercing device includes an elongated portion, a manipulation portion, and a hook portion. The hook portion is positioned proximate to the stomach of and the piercing device is manipulated such that the hook portion retracts a portion of stomach tissue proximate to the distal esophagus to form a fold of tissue having a first layer and a second layer. A securing device is passed into the esophagus of the patient, wherein the securing device includes a connector, a manipulation portion, and a securing mechanism. The securing mechanism is located proximate to the fold of stomach tissue of the patient retracted by the piercing device. The first and second layers of the fold are secured together utilizing the securing mechanism. The securing mechanism places a securing device, such as a biocompatible staple, rivet, locking device or stitch, through the layers of the fold, thereby forming a valve about the distal esophagus such that flow of gastric juices into the esophagus of the patient is substantially reduced. Optionally, one or more tubes having one or more lumens can be inserted into the esophagus of the patient for facilitating passage of the piercing device and/or securing devices into the stomach. Biocompatible locking devices and piercing devices are also described.

24 Claims, 5 Drawing Sheets

METHODS AND DEVICES FOR GASTROESOPHAGEAL REFLUX REDUCTION

BACKGROUND

Gastroesophageal reflux disease (GERD) is one of the most common upper-gastrointestinal disorders in the western world, with a prevalence of approximately 360 cases per 100,000 population per year. Approximately 25% of individuals with GERD will eventually have recurrent, progressive disease and are candidates to undergo antireflux surgical procedures for effective long term therapy. Typically an individual afflicted with GERD can control the discomfort associated with the disease by over-the-counter antacids. However, for the more chronic sufferer, prescription drugs are prescribed which can cost as much as $2,000 per year and are one of the most common treatments for GERD. It is estimated that the total direct and indirect costs of GERD prevention and treatment are estimated at $101 billion dollars a year for the United States alone.

GERD is a condition in which acids surge upward from the stomach into the esophagus, the food tube connecting the back of the throat to the stomach. Backflow of acid into the esophagus makes it raw, red and inflamed, producing the condition known as esophagitis; it also causes the painful, burning sensation behind the breastbone known as heartburn. Backflow or reflux of acid can occur when the sphincter or band muscle at the lower end of the esophagus fails to stay closed. This sphincter is called the lower esophageal sphincter (LES). The LES acts as a valve to the stomach, remaining closed until the action of swallowing forces the valve open to allow food to pass from the esophagus to the stomach. Normally the valve closes immediately after swallowing to prevent stomach contents from surging upward. When the LES fails to provide that closure, stomach acids reflux back into the esophagus, causing heartburn.

Various therapies to alleviate the symptoms of esophagitis include loss weight if the individual is overweight, not wearing tight clothing that constricts the stomach and not eating for at least three or four hours before lying down. Other non-drug treatments include avoiding foods that tend to open the LES. These foods include caffeinated beverages, such as coffee, tea and sodas; chocolate; fatty foods and peppermint.

When non-drug treatments are not enough, the individual can take an over-the-counter antacid for the occasional case of heartburn, such as MAALOX®. Also available are over-the-counter acid blockers like TAGAMET HB®, PEPCID®, AXID AR® or ZANTAC 75®. These drugs serve to block the release of acid into an individual's stomach.

Prescription strength versions of the acid blockers available. Additionally, there are other medicines that help empty the stomach of food and reduce the chances of reflux. These medicines are known as pro-kinetic drugs and include PROPULSID® (cisapride) and REGLAN® (metoclopramide).

An additional class of medicaments useful in combating esophagitis are known as proton pump inhibitors. These drugs act to block the molecular "pump" that produces acid in the stomach. These drugs include PRILOSEC (omeprazole) and PREVACID (lansoprazole). Proton pump inhibitors are typically used only in severe cases of esophagitis. They are the strongest known medicines available to counter severe symptoms of esophagitis. Typically, a physician will prescribe a combination of a proton pump inhibitor with a pro-kinetic drug, such as for example, the combination of PRILOSEC and PROPULSID.

For that percent of the population whose esophagitis does not fully respond to any prescription treatment, surgery is an option. The general approach for corrective surgery involves creating a new valve or tightening the existing valve. This procedure is known as "fundoplication" and is used to prevent the back flow of stomach acids into the esophagus. Various fundoplication procedures have been developed to correct GERD and are known as Nissen fundoplication, Belsey Mark IV repair, Hill repair and Dor repair. Each surgical procedure has its own unique attributes; however, each requires an invasive surgical procedure, whereby the individual must endure trauma to the thoracic cavity. The individual remains hospitalized after the procedure for about six to ten days.

Each of the surgical procedures were designed with an emphasis on GERD being consistent with a physiologic abnormality secondary to hypertension of the lower esophageal sphincter (LES) and not as the result of an anatomic abnormality. Early on it was not recognized that restoration of normal function between the esophagus and the gastrointestinal tract was a prerequisite of successful antireflux procedures and not just simple restoration of the individual's normal anatomy.

For example, the Nissen fundoplication technique involves enveloping the lower esophagus with the gastric fundus by suturing the anterior and posterior fundal folds about the esophagus. Modifications of this procedure include narrowing of the esophageal hiatus posterior to the esophagus, anchoring of the fundoplication to the preaortic fascia and surgical division of the vegas nerve. The degree of the fundal wrap can be modified to incompletely encircle the esophageal tube to avoid gas float syndrome and has also been modified to include a loose wrap. Similarly, the Belsey Mark IV repair, Hill repair and Dor repair are directed to modifications for encirclement of the esophageal tube by fascia.

Complications of these fundoplication procedures include the inability to belch or vomit, dysphagia, gastric ulcer, impaired gastric emptying and slippage of the repair that may foil the best surgical results. Therefore, the fundoplication procedures have been modified to adjust the length and tension of the wrap, include or exclude esophageal muscle in the sutures and leaving the vagus nerves in or out of the encirclement.

A relatively new fundoplication technique is known as Nissen fundoplication laparoscopy. In contrast to the traditional Nissen fundoplication procedure, which requires a 6 to 10 inch incision and a 6 to 10 day hospital stay with up to 8 weeks of recovery at home, the laparoscopy technique is performed through 4 to 6 tiny openings about the thoracic cavity. One opening is generally at the navel and the others are about the abdomen. Each incision is less than an inch in diameter. A surgeon inserts tubes called trocars into the body and passes a telescope-like instrument, called a laparoscope, which is connected to a camera and a video screen, through a trocar. The surgeon performs the fundoplication, constricting the esophagus much like the traditional Nissen fundoplication procedure. After the surgery is complete there is no large incision and most patients experience less discomfort than a traditional Nissen fundoplication procedure. Patients tend to leave the hospital in two days and can return to work and other activities within a week or two.

An alternative surgical procedure/device described in U.S. Pat. Nos. 3,875,928; 4,271,827; 4,271,828; and 5,006,106, collectively known as the Angelchik antireflux prosthesis (AAP), is also available for treatment of severe GERD. This procedure employs insertion of a donut-shaped prosthesis through an incision made in the abdomen. The prosthesis is placed about the intra-abdominal esophagus. A tape is passed around the esophagus and tied to the prosthesis to pull the prosthesis into position. The tape ends are tied and connected by a hemostasis clip used to secure the tightened ends of the tape. One disadvantage of the AAP is that the device tends to migrate from its original placement. This migration often times causes obstruction of the stomach, and therefore, requires repeated surgery to correct placement of the AAP. Another disadvantage is that the prosthesis cannot be reinflated if a loss of fluid occurs.

Accordingly, an object of this invention is to provide a minimally invasive method and a device for reducing gastroesophageal reflux in a patient.

A further object of this invention is to provide a biocompatible locking device for securing a fold of stomach tissue, such that a valve is created which substantially reduces the flow of gastric juices into the esophagus.

Another object of this invention is to provide a piercing device for retracting a portion of stomach tissue of a patient, such that a valve or flap is created which substantially reduces the flow of gastric juices into the esophagus.

Other general and specific objects of the invention will in part be obvious and will in part appear hereinafter.

SUMMARY OF THE INVENTION

The present invention relates to methods and devices for reducing gastroesophageal reflux in a patient.

In one aspect, the present invention provides methods for reducing gastroesophageal reflux in a patient. One method includes passing a piercing device into the esophagus of a patient. The piercing device includes an elongated portion, a manipulation portion, and a hook portion, wherein the manipulation portion is disposed at a first end of the elongated portion and the hook portion disposed at a second end of the elongated portion. The hook portion is positioned proximate to the stomach and the piercing device is manipulated such that the hook portion retracts a portion of stomach tissue proximate to the distal esophagus to form a fold of tissue having a first layer and a second layer.

A securing device is passed into the esophagus of the patient, wherein the securing device includes a connector, a manipulation portion, and a securing mechanism. The manipulation portion is disposed at a first end of the connector and the securing mechanism is disposed at a second end of the connector, such that the securing mechanism is located proximate to the fold of stomach tissue of the patient retracted by the piercing device. The first and second layers of the fold are secured together utilizing the securing mechanism. The securing mechanism places a securing means, such as a biocompatible staple, rivet, locking device or stitch, through the layers of the fold, thereby forming a valve about the distal esophagus such that flow of gastric juices into the esophagus of the patient is substantially reduced. Optionally, one or more tubes having one or more lumen can be inserted into the esophagus of the patient for facilitating passage of the piercing device and/or securing devices through the esophagus and into the stomach.

Another method includes passing a piercing device into the esophagus of a patient. The piercing device includes an elongated portion, a manipulation portion and a biocompatible locking device. The manipulation portion is disposed at a first end of the elongated portion and the biocompatible locking device is disposed at a second end of the elongated portion, such that the biocompatible locking device is located proximate to the stomach of the patient. The piercing device is manipulated such that the biocompatible locking device retracts a portion of stomach tissue proximate to the distal esophagus to form a fold of tissue having a first layer and a second layer. The first and second layers of the fold are secured together utilizing the biocompatible locking device, thereby forming a valve about the distal esophagus such that flow of gastric juices into the esophagus of the patient is substantially reduced. Optionally, a tube having an inner lumen can be used to pass the piercing device into the patients stomach.

In another aspect, the invention provides a biocompatible locking device for securing a fold of stomach tissue. The device includes a head portion having a sharpness sufficient to perforate stomach tissue, a shaft portion having a length sufficient to extend through a first and a second layer of stomach tissue, and a base portion, wherein the shaft portion connects the base portion to the head portion. The head portion has a shape and a size such that the head portion can pass through the first and the second layers of tissue in a first direction and is retained by the first and the second layers of tissue when force is applied in a second opposing direction. The base portion has a shape and size such that the base portion is retained from passing through a hole in the first and second layers formed by the head portion passing through the first and second layers. The head portion and base portion provide a substantially permanent attachment of the first layer to the second layer. For example, the head portion of the device can be in the shape of a wedge.

In yet another aspect, the present invention provides a piercing device for retracting a portion of stomach tissue of a patient. The device includes a manipulation portion, an elongated portion and a hook portion. The elongated portion connects the manipulation portion to the hook portion, wherein the hook portion has a shape for retracting a portion of the stomach tissue to form a fold of tissue. The manipulation portion has a shape for facilitating movement of the elongated portion to manipulate the piercing device to retract the portion of stomach tissue with the hook portion. The hook portion can be biocompatible and/or biodegradable.

In still another aspect, the present invention provides a securing device for substantially permanently attaching a first layer of stomach tissue to a second layer of stomach tissue. The securing device includes a manipulation portion, a connector and a securing mechanism. The connector connects the manipulation portion to the securing mechanism, wherein the securing mechanism provides a securing means for substantially permanently attaching a first and a second layer of tissue together. The manipulation portion has a shape for facilitating movement of the securing mechanism to secure the first and second layers of stomach tissue.

This invention provides several advantages over known methods and devices for reducing gastroesophageal reflux in a patient. For example, the method and device do not require surgery for implantation. Therefore, patient compliance and patient comfort is greatly enhanced. Consequently, the method can be performed in a physician's office or as an out-patient ambulatory procedure, whereby the patient does not require general anesthesia. Further, the present invention provides a method and device for reducing gastroesophageal reflux that includes a biodegradable hook portion. Therefore, the biodegradable hook portion which connects portions of the stomach tissue to form a fold of tissue to reduce the flow of gastric juices into the esophagus will biodegrade over a sufficient period of time. As a consequence of this, the patient is not faced with the possibility of retaining an internal foreign object for an indefinite period of time which may cause unknown complications and/or discomfort to the patient.

DETAILED DESCRIPTION OF THE INVENTION

The invention provides to methods and devices for reducing gastroesophageal reflux in a patient.

In one aspect, the present invention provides methods for reducing gastroesophageal reflux in a patient. One method includes passing a piercing device into the esophagus of a patient. The piercing device includes an elongated portion, a manipulation portion, and a hook portion, wherein the manipulation portion is disposed at a first end of the elongated portion and the hook portion disposed at a second end of the elongated portion. The hook portion is positioned proximate to the stomach and the piercing device is manipulated such that the hook portion retracts a portion of stomach tissue proximate to the distal esophagus to form a fold of tissue having a first layer and a second layer.

A securing device is passed into the esophagus of the patient, wherein the securing device includes a connector, a manipulation portion, and a securing mechanism. The manipulation portion is disposed at a first end of the connector and the securing mechanism is disposed at a second end of the connector, such that the securing mechanism is located proximate to the fold of stomach tissue of the patient retracted by the piercing device. The first and second layers of the fold are secured together utilizing the securing mechanism. The securing mechanism places a securing means, such as a biocompatible staple, rivet, locking device or stitch, through the layers of the fold, thereby forming a valve about the distal esophagus such that flow of gastric juices into the esophagus of the patient is substantially reduced. For example, the securing step forms a valve having a surface area of less than about 2.5 cm². Additionally, the method provides that the valve formed has sufficient flexibility to allow release of stomach gases past the valve while substantially reducing flow of gastric juices into the esophagus.

In a preferred embodiment of the invention, the securing step includes utilizing the securing device to substantially permanently attach the first layer to the second layer. The securing step includes substantially permanently stapling the first and second layers of the fold with at least one biocompatible staple or by inserting a biocompatible locking device through the layers.

In one embodiment, an endoscope is also inserted into the esophagus of the patient. This endoscope can include means for viewing the stomach and esophagus of the patient. Suitable means for viewing include those known in the art including television array and video array. Suitable examples of endoscopes include pilling rigid dilating esophagoscopes or bard esophageal overtubes.

Optionally, one or more tubes each having one or more lumen can be inserted into the esophagus of the patient for facilitating passage of the piercing device and/or securing devices through the esophagus and into the stomach.

In another aspect of the invention, the method includes passing a piercing device into the esophagus of a patient. The piercing device includes an elongated portion, a manipulation portion and a biocompatible locking device. The manipulation portion is disposed at a first end of the elongated portion and the biocompatible locking device is disposed at a second end of the elongated portion, such that the biocompatible locking device is located proximate to the stomach of the patient. The piercing device is manipulated such that the biocompatible locking device retracts a portion of stomach tissue proximate to the distal esophagus to form a fold of tissue having a first layer and a second layer. The first and second layers of the fold are secured together utilizing the biocompatible locking device, thereby forming a valve about the distal esophagus such that flow of gastric juices into the esophagus of the patient is substantially reduced.

The term "endoscope" is art recognized and is intended to include, but is not limited to, instruments equipped with a lighting attachment and lens system for visual examination of the interior of the body or a body cavity. Suitable examples include substantially rigid esophagoscopes and substantially rigid gastroscopes.

The term "piercing device" is intended to encompass a combination of parts which function as a single unit. For example, a piercing device can include an elongated portion, a manipulation portion and a hook portion, which when acting as a single unit and are contacted against tissue with sufficient force, pierce or penetrate the tissue to a degree which allows the tissue to be readily manipulated.

The term "elongated portion" is intended to include that portion of a piercing device which connects a manipulation portion to a hook portion. The elongated portion is of sufficient length to pass through the oral cavity, through the esophagus and into the stomach. Typically an elongated portion is between about 15 mm and about 40 mm in length and has a diameter of between about 2 mm and about 4 mm. Suitable examples of materials used for the elongated portion of the piercing device include polyethylene. In one embodiment, the material is chosen such that the elongated portion can be readily separated from a hook portion and the manipulation portion of the piercing device. For example, the tensile strength of the elongated portion can be chosen such that the point of attachment of the hook portion and elongated portion can be "snapped" by enough force in excess of the tensile strength of the elongated portion, e.g., a firm jerk, once the hook is secured into or through stomach tissue.

The term "hook portion" is intended to include that portion of the piercing device which is disposed at an end of the elongated portion which is opposite to the manipulation portion and is inserted through the esophagus and into the stomach of a patient. The hook portion includes a sharpened end, which when manipulated via the manipulation portion and the elongated portion, can retract a portion of the stomach tissue. Typically, the hook portion has a curvature of 150° and a length of between about 0.5 and about 1.5 cm and a diameter of between about 0.2 mm and about 0.5 mm. The hook portion can further include barbs and/or points to facilitate in retaining tissue. Suitable materials from which the hook portion is fashioned include polyethylene, polyglactin and polyglycolic acid, e.g., the hook portion can be biodegradable or biocompatible or both. The hook portion can be attached to the elongated portion via suture for separation/disconnection from the elongated portion. In a preferred embodiment, the hook portion is manipulated such that the folds of stomach tissue are substantially permanently secured by the hook portion, e.g., the hook portion retains the tissue fold and remains attached.

The term "securing device" is intended to encompass a combination of parts which function as a single unit. For example, a securing device can include a connector, a manipulation portion and a securing mechanism, which when acting as a single unit are positioned such that the securing mechanism is positioned about folds of stomach tissue, and inserts a securing means. In a preferred embodiment, the securing mechanism is manipulated such that the folds of stomach tissue are substantially permanently secured by a securing means associated with the securing mechanism, such as a staple, e.g. the securing mechanism can be a staple gun attached to the connector. Alternatively, the securing mechanism can act as the securing means and itself be released from the connector to secure the folds of stomach tissue. Preferred securing mechanisms which can be released from the connector include biocompatible hooks or a biodegradable/biocompatible locking device described infra.

The term "connector" is intended to include that portion of a securing device which connects the manipulation portion to the securing mechanism. The connector is of sufficient length to pass through the oral cavity, through the esophagus and into the stomach. Typically a connector is between about 15 mm and about 40 mm in length and has a diameter of between about 0.5 mm and about 2 mm. Suitable examples of materials used for the connector of the securing device include polyethylene. The tensile strength of the connector can be chosen such that the point of attachment of the securing device and connector can be "snapped" by enough force in excess of the tensile strength of the connector portion, e.g., a firm jerk, once the securing device is secured into or through stomach tissue.

The term "manipulation portion" is intended to include that portion of the piercing device which is disposed at the end of an elongated portion which is opposite to a biocompatible hook portion and is maintained outside of an endoscope. The manipulation portion allows an operator, such as a physician, to position the biocompatible hook portion via the elongated portion. The manipulation portion also provides a means for steering to attach the hook portion. The manipulation portion also includes that portion of a securing device which is disposed at the end of a connector which is opposite to a securing mechanism and is maintained outside of an endoscope.

The term "biocompatible" as that term is used herein, means exhibition of essentially no cytotoxicity while in contact with body fluids or tissues. "Biocompatibility" also includes essentially no interactions with recognition proteins, e.g., naturally occurring antibodies, cell proteins, cells and other components of biological systems.

The hook portion of a piercing device or the securing mechanism of a securing device, e.g. biocompatible locking device, can be released from an elongated portion or a connector, respectively, by various methods. In one embodiment, an upper portion of the hook portion or securing mechanism, at the point of attachment to the elongated portion or connector, has external threading. The elongated portion or the connector has internal threading which accepts the externally threaded hook portion or securing mechanism. Rotation of the elongated portion or the connector via the manipulation portion in the direction opposite to the external threading will release the hook portion or the securing mechanism once positioned within the stomach tissue fold. Alternatively, quick connects such as those known in the art can be employed for the release of the hook portion or securing mechanism.

The phrase "flow of gastric juices into the esophagus is substantially reduced" is intended to include inhibition or prevention of the flow of gastric juices from the stomach into the esophagus, such that esophagitis is greatly diminished or ceases to exist. In one preferred embodiment, the flow of gastric juices into the esophagus has been decreased by at least about 75 percent and more preferably at least about 90 percent. In a most preferred embodiment, the flow of gastric juices into the esophagus has been decreased by at least about 99 percent, such that relief of esophagitis is regarded as complete.

The phrase "substantially permanently attach" is intended to mean that a first and second layer of the stomach is attached for a sufficient period of time to allow the stomach to heal; generally, this period of time is indefinite. During this time, the first and second layers remain connected in a valve or fold and are not separated under daily use. However, if a need arises to remove the securing mechanism, such as a locking device, or hook portion, a removal device can be inserted into the patient's esophagus to remove the object. For example, where the hook has external threading, a device as described supra could be reinserted into the stomach and reattached to the threaded portion of the hook. Alternatively, where the securing mechanism, e.g. hook portion, is biodegradable, the period of time required for biodegradation to occur is generally between 12–24 months, most preferably between 6–12 months.

The term "biodegradable," as that term is used herein, means materials, such as polymers, which are degraded in response to contact with body fluid while implanted in vivo. Examples of biodegradation processes include hydrolysis, enzymatic action, oxidation and reduction. Suitable conditions for hydrolysis, for example, include exposure of the biodegradable materials to gastric fluids at a temperature and a pH of that normally found in a human stomach.

The term "substantially rigid," as that term is used herein, means that a device is made of a material which retains its form while having enough pliability to be inserted through the esophagus without bruising, cutting or damaging the esophagus. In preferred embodiments, the material which comprises the elongated portion and/or connector is rigid enough to not require the use of a tube to guide the piercing device or the securing device through a patient's esophagus.

The figures are presented for the purpose of illustrating the practice of the invention, so as to enable those skilled in the art to understand and practice it, but are not intended as limitations on the scope of the invention. In these figures, like reference characters depict the same devices in several views.

Figure 1:
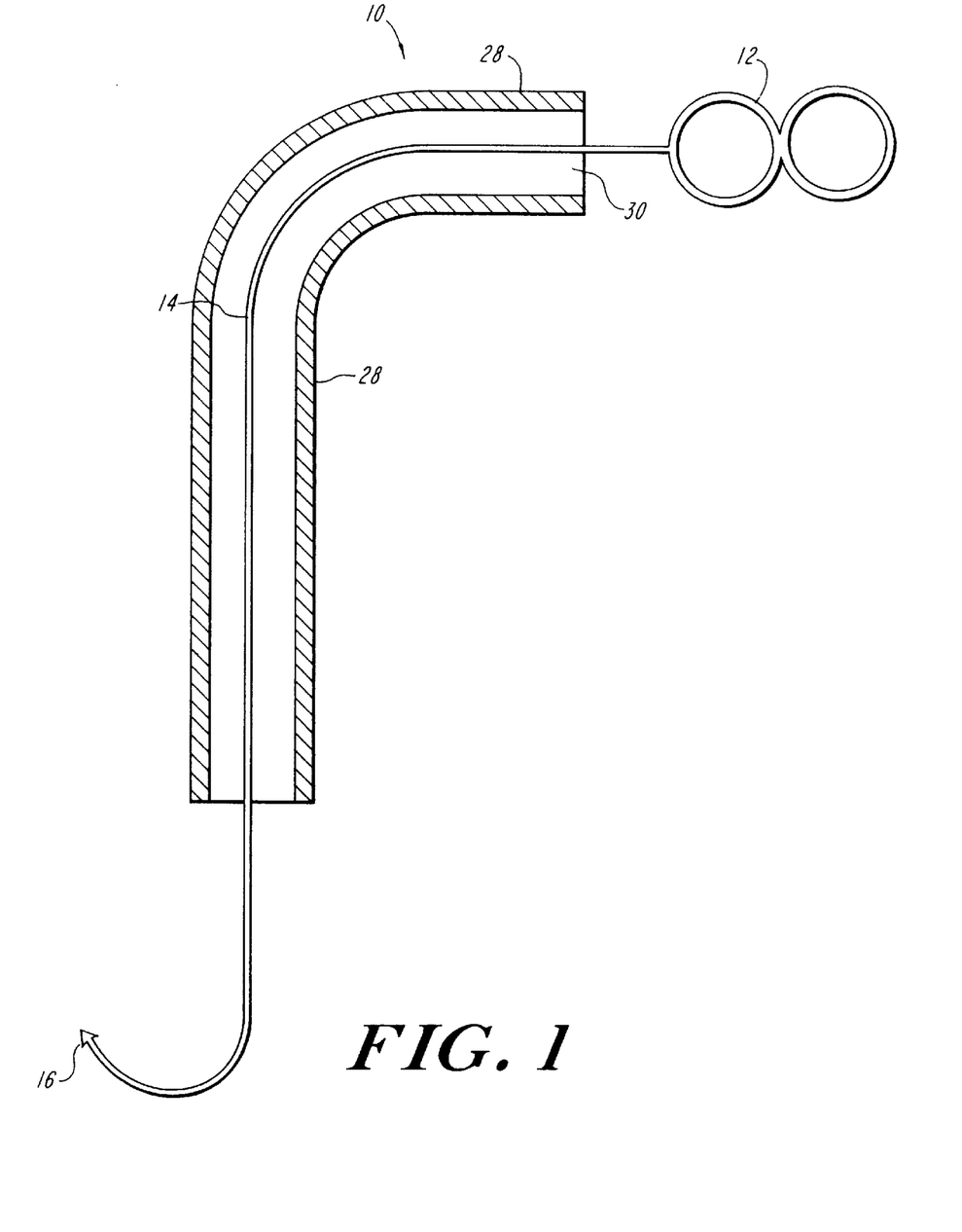
FIG. 1 depicts the piercing device of the invention.

In one aspect, as depicted in FIG. 1, the invention provides a piercing device 10 for retracting a portion of stomach tissue of a patient. The device includes a manipulation portion 12, an elongated portion 14 and a biocompatible hook portion 16. The elongated portion 14 connects the manipulation portion 12 to the biocompatible hook portion 16. The biocompatible hook portion 16 has a shape for retracting a portion of stomach tissue to form a fold of tissue. The manipulation portion 12 has a shape for facilitating movement of the manipulation portion 12 to manipulate the piercing device 10 to retract the portion of stomach tissue with the biocompatible hook portion 16. In a preferred embodiment, the hook portion is biocompatible and biodegradable.

In another aspect, as shown in FIGS. 2a–2e, the invention provides a biocompatible locking device 18 for securing a fold of stomach tissue. The locking device 18 includes a head portion 20, a shaft portion 22 and a base portion 24. In one preferred embodiment, the biocompatible locking device 18 is biodegradable.

Figure 2A:
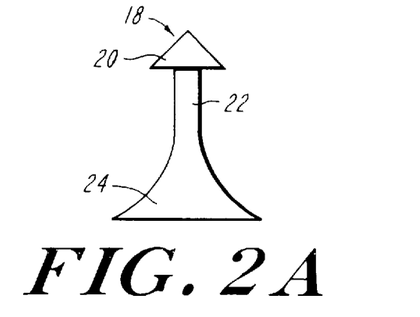
FIGS. 2A–2E depict various embodiments of locking devices.
Figure 2B:
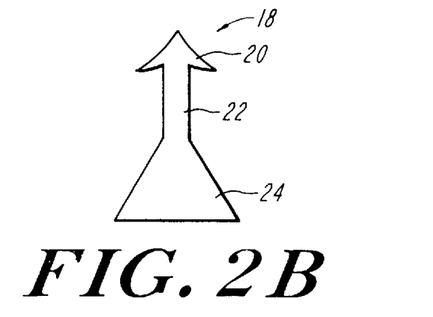
Figure 2C:
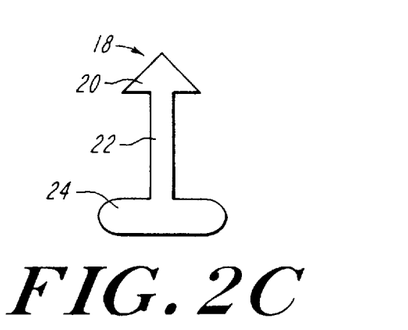

The head portion 20 has a sharpness sufficient to perforate stomach tissue. It also has a shape and a size suitable to pass through a first and second layer of stomach tissue in a first direction and which is retained by the first and second layers if pulled in an opposing direction. Typically, the head portion 20 has a pin shape and is about 3 centimeter in length. The thickness of the head portion 20 can vary from between about 1 mm to about 2 mm, preferably between about 1 mm and about 1.5 mm. In one embodiment, the head portion 20 has a shape of a wedge (FIGS. 2a and 2b). The biocompatible locking device is designed to pierce the stomach while preventing gastric juice extravasation.

Figure 2D:
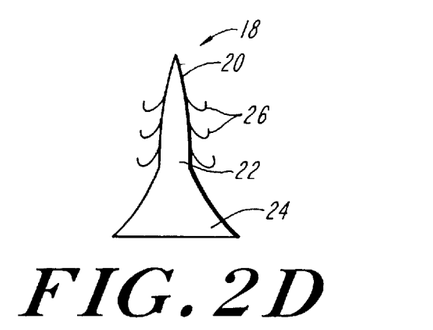

The shaft portion 22 has a length sufficient to extend through the first and second layer of stomach tissue and to connect the base portion 24 to the head portion 20. A suitable length is from about 30 mm to about 50 mm, preferably from about 30 mm to about 35 mm. In one embodiment as shown in FIG. 2d, shaft portion 22 includes barbs 26 to facilitate retaining the layers of tissue.

Figure 2E:
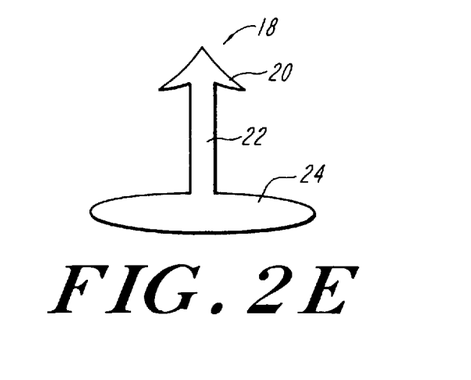

The base portion 24 has a shape and size such that the base portion 24 is retained from passing through a hole in the first and second layers of tissue formed by the head portion 20 passing through the first and second layers. The head portion 20 and base portion 24 thereby provide a substantially permanent attachment of the first layer to the second layer. The base portion 24 can be fluted, flared, or perpendicularly attached to the shaft portion 22, as shown in FIGS. 2a–2e, thereby providing an anchoring means to retain the first and second layers. In one embodiment, the base portion 24 is a circular flat disc and has a circumference at least equal to the widest portion of the head portion, more preferably, the circumference is at least twice the widest portion of the head portion, such as shown in FIG. 2e.

Figure 3:
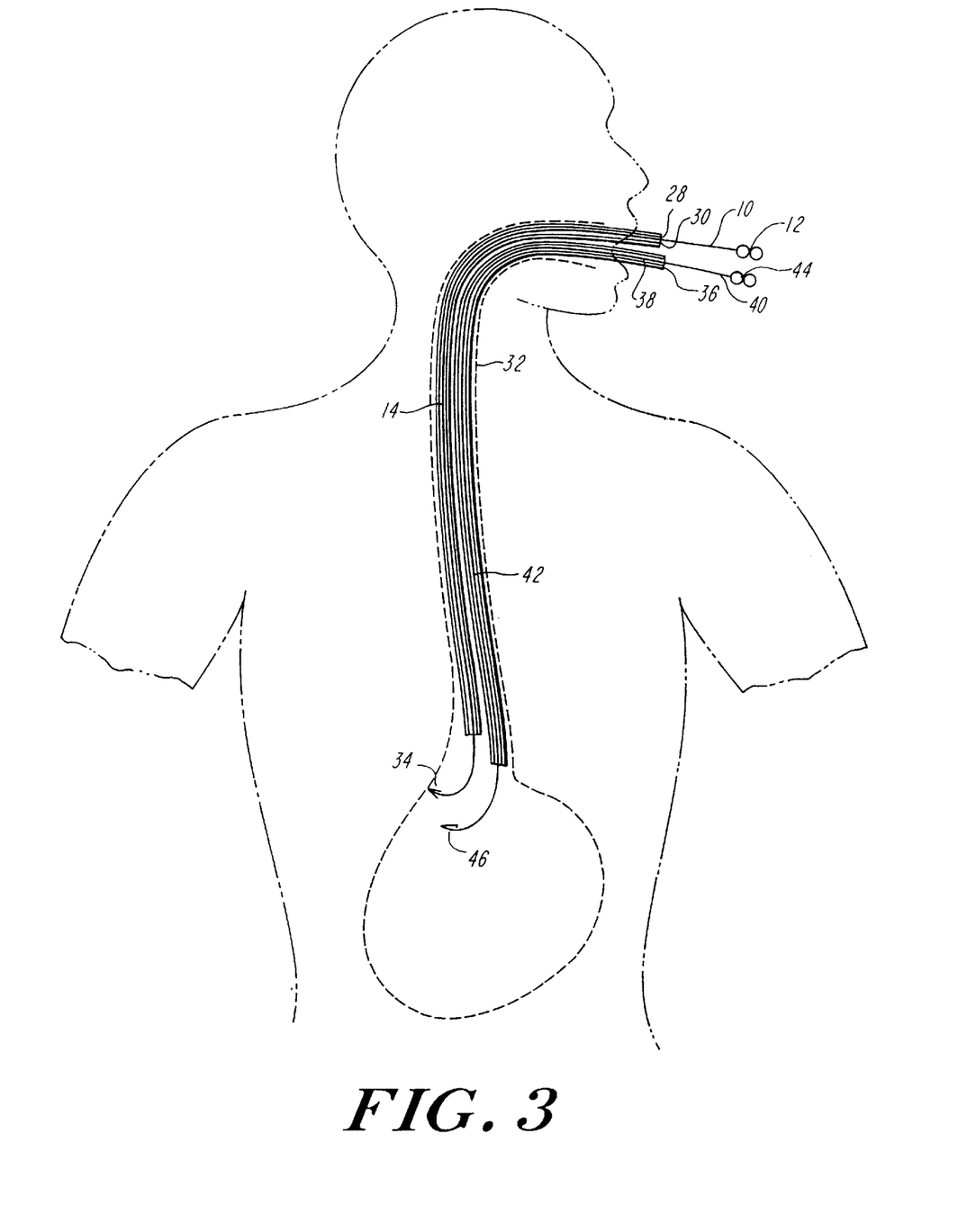
FIG. 3 is a cross-sectional view of the placement of a piercing device and a securing device with two endoscopes.

As shown in FIG. 3, a first tube 28 (optional) having a first inner lumen 30 is inserted into the esophagus 32 of a patient. At least one piercing device 10 is passed through the first inner lumen 30. The piercing device 10 includes an elongated portion 14, a manipulation portion 12, and a hook portion 34. The manipulation portion 12 is disposed at a first end of the elongated portion 14 which is maintained outside of the first inner lumen 30. The hook portion 34 is disposed at a second end of the elongated portion 14 such that the hook portion 34 is positioned proximate to the stomach of the patient. The piercing device 10 is manipulated such that the hook portion 34 retracts a portion of stomach tissue proximate to the distal esophagus thereby forming a fold of tissue having a first layer and a second layer (not shown).

A second tube 36 (optional) is inserted into the esophagus 32 of the patient. At least one securing device 40 is passed through the second inner lumen 38 of second tube 36. The securing device 40 includes a connector 42, a manipulation portion 44 and a securing mechanism 46. The first and second layers of the fold are secured together by a securing means of (not shown) the securing mechanism 46, thereby forming a valve about the distal esophagus such that flow of gastric juices into the esophagus of the patient is substantially reduced. Hook portion 34 is removed from the fold of tissue. The piercing device 10, the securing device 40 and the tubes 28 and 36 are then removed from the esophagus.

Figure 4:
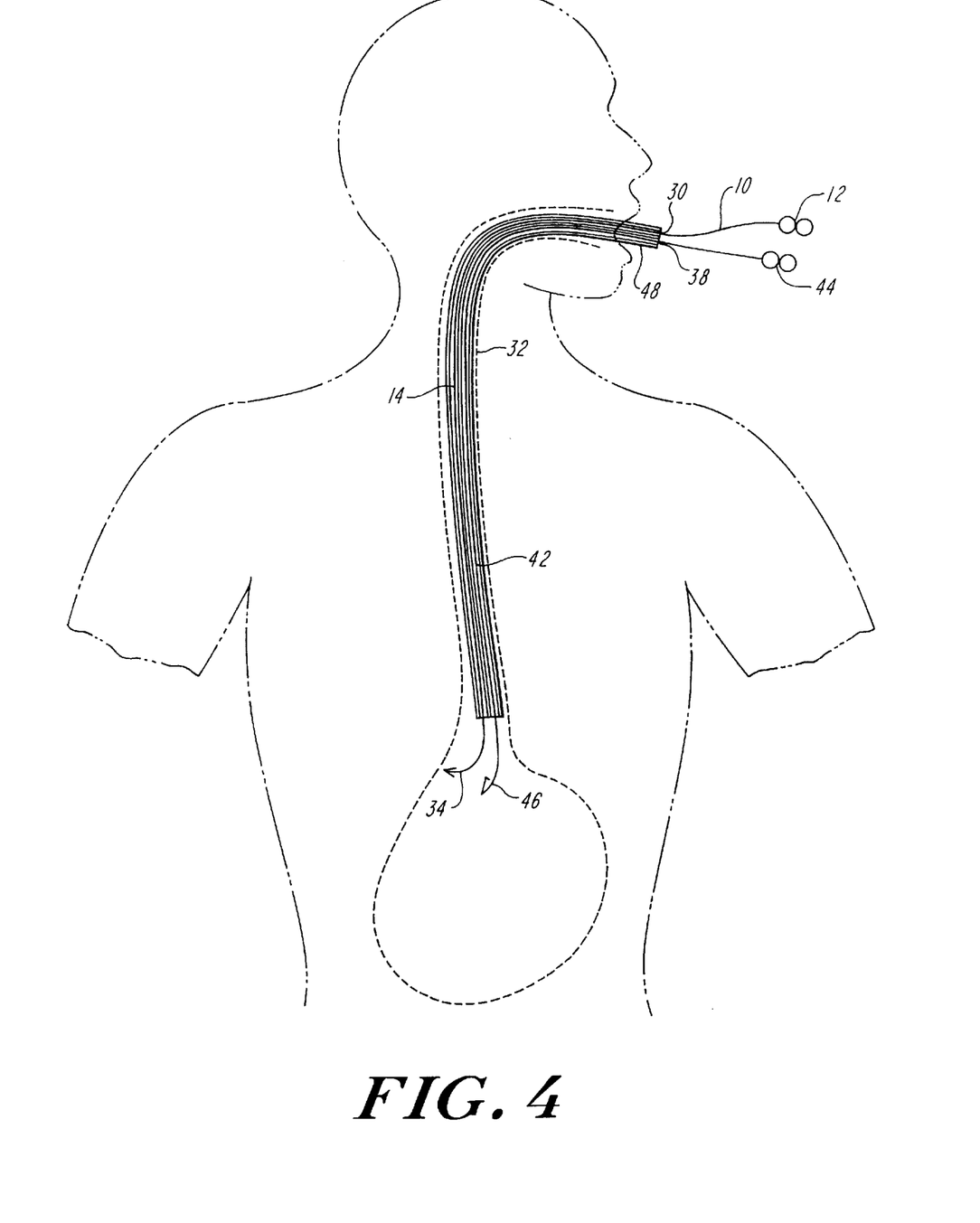
FIG. 4 is a cross-sectional view of the placement of a piercing device and a securing device with a single endoscope.

FIG. 4 substantially incorporates the description of FIG. 3 with the following differences. A tube 48 (optional) which includes a first inner lumen 30 and a second inner lumen 38 is inserted into the esophagus 32 of the patient. At least one piercing device 10 is passed through the first inner lumen 30 with the piercing device 10 having an elongated portion 14, a manipulation portion 12, and a hook portion 34. The manipulation portion 12 is disposed at a first end of the elongated portion 14 and is maintained outside of the first inner lumen 30. The hook portion 34 is disposed at a second end of the elongated portion 14 such that the hook portion 34 is positioned proximate to the stomach of the patient. The piercing device 10 is manipulated such that the hook portion 34 retracts a portion of stomach tissue proximate to the distal esophagus thereby forming a fold of tissue having a first layer and a second layer (not shown).

At least one securing device 40 is passed through the second inner lumen 38 of the tube 48 with the securing device 40 having a connector 42, a manipulation portion 44, and a securing mechanism 46. The manipulation portion 44 disposed at a first end of the connector 42 and is maintained outside of the second inner lumen 38 of the tube 48. The securing mechanism 46 is disposed at a second end of the connector 42 such that the securing mechanism 46 is positioned proximate to the fold of tissue of the patient.

The first and the second layers of the fold are secured together by a securing means (not shown) of the securing mechanism 46, thereby forming a valve about the distal esophagus such that the flow of gastric juices into the esophagus 32 of the patient is substantially reduced. The hook portion 34 is removed from the fold of tissue. The piercing device 10, the securing device 40 and the tube 48 are then removed from the esophagus 32.

Figure 5:
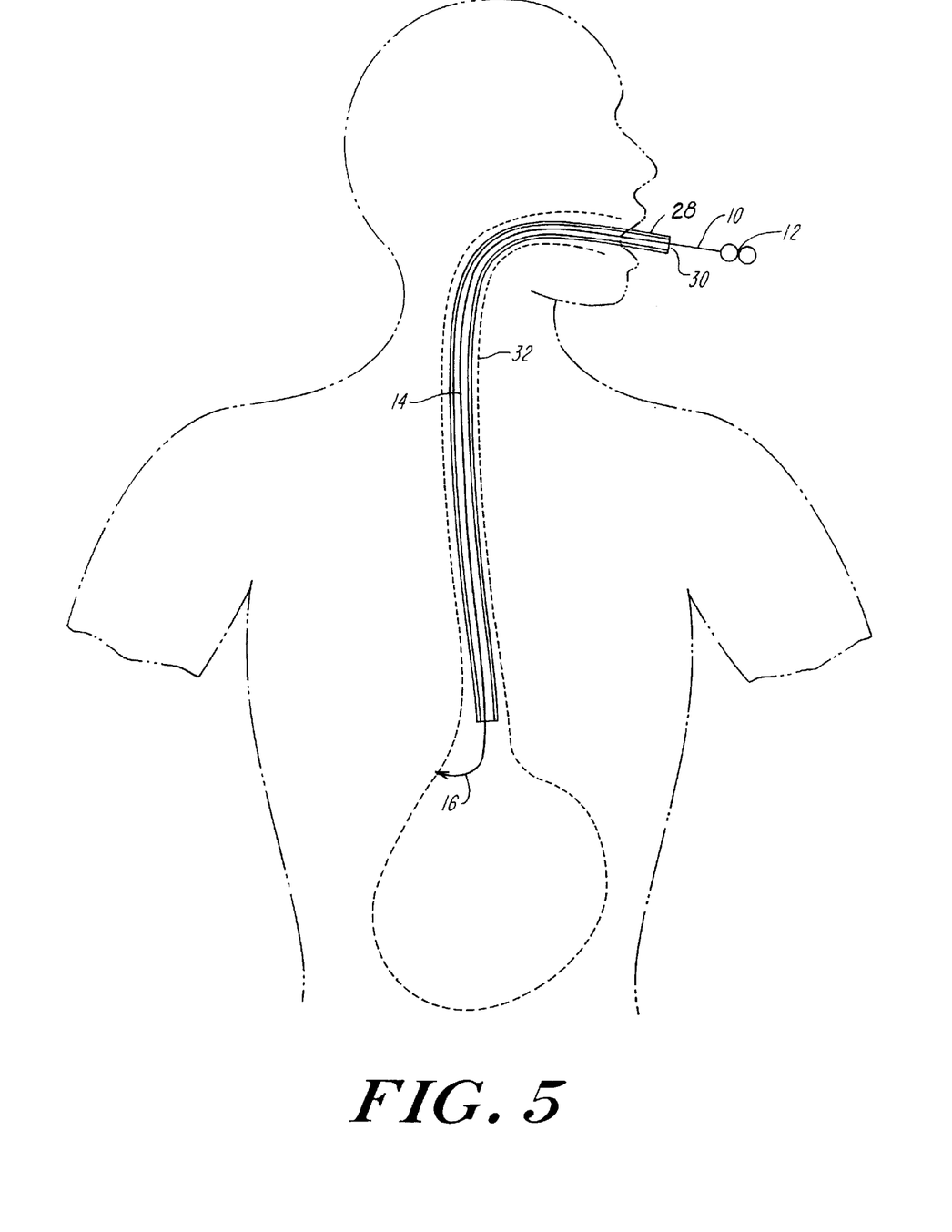
FIG. 5 is a cross-sectional view of the placement of a piercing device.

FIG. 5 depicts a tube 28 (optional) having an inner lumen 30 in the esophagus 32 of a patient. At least one piercing device 10 is passed through the inner lumen 30 with the piercing device 10 having an elongated portion 14, a manipulation portion 12, and a biocompatible hook portion 16. The manipulation portion 12 is disposed at a first end of the elongated portion 14 and is maintained outside of the first inner lumen 30. The biocompatible hook portion 16 is disposed at a second end of the elongated portion 14 such that the biocompatible hook portion 16 is positioned proximate to the stomach of the patient.

The piercing device 10 is manipulated such that the biocompatible hook portion 16 retracts a portion of stomach tissue proximate to the distal esophagus to form a fold of tissue having a first layer and a second layer (not shown). The first and second layers of the fold are secured together by the biocompatible hook portion 16, thereby forming a valve about the distal esophagus such that flow of gastric juices into the esophagus of the patient is substantially reduced. The elongated portion 14 of the piercing device 10 is released from the biocompatible hook portion 16 and the elongated portion 14 and tube 28 are removed from the esophagus 32.

The contents of all references and published patent applications, cited throughout this application are hereby incorporated by reference.

Equivalents

Those skilled in the art will know, or be able to ascertain, using no more than routine experimentation, many equivalents to the specific embodiments of the invention described herein. These and all other equivalents are intended to be encompassed by the following claims.

What is claimed is:

1. A method for reducing gastroesophageal reflux in a patient comprising:
   a) passing a piercing device into the esophagus of a patient, said piercing device having an elongated portion, a manipulation portion, and a hook portion, said manipulation portion disposed at a first end of said elongated portion and said hook portion disposed at a second end of said elongated portion such that said hook portion is positioned proximate to the stomach of said patient;
   b) manipulating said piercing device such that said hook portion retracts a portion of said securing device of stomach tissue proximate to the distal esophagus to form a fold of tissue having a first layer and a second layer;
   c) passing a securing device into the esophagus of said patient, said securing device having a connector, a manipulation portion, and a securing mechanism, said manipulation portion disposed at a first end of said connector and said securing mechanism disposed at a second end of said connector such that said securing mechanism is proximate to said fold of tissue of said patient; and
   d) securing said first and said second layers of said fold together utilizing said securing mechanism, thereby forming a valve about the distal esophagus such that flow of gastric juices into the esophagus of the patient is substantially reduced.

2. The method of claim 1, wherein the securing step comprises stapling said first layer to said second layer with at least one biocompatible staple, said staple substantially permanently attaching said first layer to said second layer.

3. The method of claim 1, wherein the securing step comprises inserting a biocompatible locking device through said first and said second layers, said biocompatible locking device substantially permanently attaching said first layer to said second layer.

4. The method of claim 1, wherein the securing step comprises forming a valve having a surface area of less than about 2.5 cm$^2$.

5. The method of claim 1, wherein the securing step comprises securing said first and second layers of said fold together to form said valve having sufficient flexibility to allow release of stomach gases past said valve while substantially reducing flow of gastric juices into the esophagus.

6. The method of claim 1, further comprising inserting a first tube having a first inner lumen into the esophagus of the patient prior to step a), such that said piercing device is passed through said first inner lumen.

7. The method of claim 6, further comprising inserting a second tube having a second inner lumen into the esophagus of the patient prior to step c), such that said securing device is passed through said second inner lumen.

8. The method of claim 1, further comprising inserting a tube having a plurality of inner lumens into the esophagus of the patient prior to step a), such that said piercing device and said securing device are passed through an inner lumen.

9. The method of claim 1, further comprising inserting an endoscope for viewing the stomach prior to either steps a), b), c), or d).

10. A method for reducing gastroesophageal reflux in a patient, comprising:
    a) passing a piercing device into the esophagus of a patient, said piercing device having an elongated portion, a manipulation portion and a biocompatible locking device, said manipulation portion disposed at a first end of said elongated portion and said biocompatible locking device disposed at a second end of said elongated portion such that said biocompatible locking device is proximate to the stomach of said patient;
    b) manipulating said piercing device such that said biocompatible locking device retracts a portion of stomach tissue proximate to the distal esophagus to form a fold of tissue having a first layer and a second layer; and
    c) securing said first and said second layers of said fold together utilizing said biocompatible locking device, thereby forming a valve about the distal esophagus such that flow of gastric juices into the esophagus of said patient is substantially reduced.

11. The method of claim 10, wherein the securing step comprises forming a valve having a surface area of less than about 2.5 cm$^2$.

12. The method of claim 10, wherein the securing step comprises securing said first and second layers of said fold together to form said valve having sufficient flexibility to allow release of stomach gases past said valve while substantially reducing flow of gastric juices into the esophagus.

13. The method of claim 10, further comprising inserting a first tube having a first inner lumen into the esophagus of the patient prior to step a), such that said piercing device is passed through said first inner lumen.

14. The method of claim 10, further comprising inserting an endoscope for viewing the stomach prior to either steps a), b), or c).

15. A biocompatible locking device for securing a fold of stomach tissue comprising:
    a head portion having a sharpness sufficient to perforate stomach tissue;
    a shaft portion having a length sufficient to extend through a first and a second layer of stomach tissue; and
    a base portion;
    wherein said shaft portion connects said base portion to said head portion;
    wherein said head portion has a shape and a size such that said head portion can pass through said first and said second layers in a first direction and is substantially retained by said first and said second layers if pulled in a second opposing direction; and
    wherein said base portion has a shape and a size such that said base portion is substantially retained from passing through a hole in said first and said second layers formed by said head portion passing through said first and said second layers, said head portion and said base portion thereby providing a substantially permanent attachment of said first layer to said second layer.

16. The device of claim 15, wherein said biocompatible locking device is biodegradable.

17. The device of claim 15, wherein said head portion has a shape of a wedge.

18. A piercing device for retracting a portion of stomach tissue of a patient comprising:
    a manipulation portion;
    an elongated portion;
    a hook portion;
    wherein said elongated portion connects said manipulation portion to said hook portion;

wherein said hook portion has a shape for retracting a portion of stomach tissue to form a fold of tissue; and wherein said manipulation portion has a shape for facilitating movement of said hook portion to retract a portion of stomach tissue.

19. The piercing device of claim 18, wherein said hook portion is biocompatible.

20. The piercing device of claim 18, wherein said hook portion is biodegradable.

21. The piercing device of claim 18, wherein said hook portion is biocompatible and biodegradable.

22. A securing device for substantially permanently attaching a first layer to a second layer of stomach tissue, comprising:

a manipulation portion;

a connector;

a securing mechanism;

wherein said connector connects said manipulation portion to said securing mechanism;

wherein said securing mechanism provides a securing means for substantially permanently attaching a first and a second layer of tissue together; and wherein said manipulation portion has a shape for facilitating movement of said securing mechanism to secure a fold of stomach tissue.

23. The device of claim 22, wherein said securing mechanism is a biocompatible staple, hook, locking device or stitch.

24. The device of claim 23, wherein said biocompatible staple, hook, locking device or stitch is biodegradable.

* * * * *